United States Patent
Winski et al.

(10) Patent No.: US 9,987,454 B2
(45) Date of Patent: Jun. 5, 2018

(54) RAINOUT PROTECTION FOR RESPIRATORY THERAPY INCLUDING HUMIDIFICATION

(71) Applicant: KONINKLIJKE PHILIPS N.V., Eindhoven (NL)

(72) Inventors: Jeffrey Ronald Winski, Irwin, PA (US); Richard Charles Dombrowski, Trafford, PA (US); Benjamin Alfred Giovannelli, Gibsonia, PA (US)

(73) Assignee: Koninklijke Philips N.V., Eindhoven (NL)

( * ) Notice: Subject to any disclaimer, the term of this patent is extended or adjusted under 35 U.S.C. 154(b) by 911 days.

(21) Appl. No.: 14/378,692

(22) PCT Filed: Feb. 21, 2013

(86) PCT No.: PCT/IB2013/051399
§ 371 (c)(1),
(2) Date: Aug. 14, 2014

(87) PCT Pub. No.: WO2013/124803
PCT Pub. Date: Aug. 29, 2013

(65) Prior Publication Data
US 2016/0015927 A1 Jan. 21, 2016

Related U.S. Application Data

(60) Provisional application No. 61/602,638, filed on Feb. 24, 2012.

(51) Int. Cl.
*H05B 3/00* (2006.01)
*A61M 16/16* (2006.01)
(Continued)

(52) U.S. Cl.
CPC ...... *A61M 16/161* (2014.02); *A61M 16/0003* (2014.02); *A61M 16/0057* (2013.01);
(Continued)

(58) Field of Classification Search
CPC .......... A61M 16/0051; A61M 16/0003; A61M 16/0057; A61M 16/06; A61M 16/1075;
(Continued)

(56) References Cited

U.S. PATENT DOCUMENTS

| | | | | |
|---|---|---|---|---|
| 4,621,632 A | * | 11/1986 | Bartels | A61M 16/1075 128/203.17 |
| 7,051,733 B2 | * | 5/2006 | Gradon | A61M 16/1075 128/203.17 |

(Continued)

FOREIGN PATENT DOCUMENTS

| | | |
|---|---|---|
| EP | 1138341 A2 | 4/2001 |
| JP | 09234247 A | 9/1997 |

(Continued)

*Primary Examiner* — Kari Rodriquez
*Assistant Examiner* — Victoria Murphy

(57) ABSTRACT

A system for providing respiratory therapy to a subject using a subject interface (180). The system responding and/or adapting to a detection of the subject exerting a heat influence on the system, e.g. the subject increasing the temperature of the subject interface. For respiratory therapy that includes the use of a humidifier (150), condensation or rainout is commonly a problem. The response and/or adaptation may inhibit condensation from forming along the subject interface.

18 Claims, 4 Drawing Sheets

(51) Int. Cl.
*A61M 16/00* (2006.01)
*A61M 16/08* (2006.01)
*A61M 16/10* (2006.01)

(52) U.S. Cl.
CPC ........ *A61M 16/024* (2017.08); *A61M 16/109* (2014.02); *A61M 16/1095* (2014.02); *A61M 16/16* (2013.01); *A61M 16/0808* (2013.01); *A61M 2016/102* (2013.01); *A61M 2205/3365* (2013.01); *A61M 2205/3368* (2013.01); *A61M 2205/36* (2013.01); *A61M 2205/505* (2013.01); *A61M 2205/581* (2013.01); *A61M 2205/582* (2013.01); *A61M 2205/587* (2013.01)

(58) Field of Classification Search
CPC ................ A61M 16/16; A61M 16/161; A61M 2205/50; A61M 2230/005; A61M 2230/50; A61M 16/1095; A61M 16/1085; A61M 16/0069; A61M 2205/3653; A61M 2205/3368; A61M 2016/003; A61M 16/08; A61M 16/0841; A61M 16/164
USPC ........................ 128/203.17, 203.27; 261/130
See application file for complete search history.

(56) References Cited

U.S. PATENT DOCUMENTS

| | | | |
|---|---|---|---|
| 2007/0051368 A1* | 3/2007 | Seakins ................. | A61M 16/08 128/203.17 |
| 2008/0190427 A1 | 8/2008 | Payton et al. | |
| 2009/0044810 A1 | 2/2009 | Kwok et al. | |
| 2010/0307495 A1 | 12/2010 | Kepler et al. | |
| 2011/0120462 A1* | 5/2011 | Tatkov .............. | A61M 16/1075 128/203.14 |

FOREIGN PATENT DOCUMENTS

| | | |
|---|---|---|
| JP | 2011125618 A | 6/2011 |
| WO | 2009022004 A2 | 2/2009 |

* cited by examiner 200, 200b 

```
┌─────────────────────────┐
│  Continued from FIG. 2A │
└─────────────────────────┘
             │
             ▼
┌──────────────────────────────────────────────────────────────────┐
│ Detect whether the current temperature is being elevated by at   │
│ least a minimum elevation level above the target temperature due │─ 220
│ to a heat influence of the subject                               │
└──────────────────────────────────────────────────────────────────┘
             │
             ▼
┌──────────────────────────────────────────────────────────────────┐
│ Control the formation of vapor to maintain the target humidity   │
│ based on the current temperature, wherein, responsive to the     │
│ detection, the formation of vapor is further controlled to       │─ 222
│ maintain the target humidity as if the current temperature were  │
│ equal to the target temperature, thereby inhibiting condensation │
│ from forming along the subject interface by the humidified,      │
│ pressurized flow of breathable gas between the pressure          │
│ generator and the airway of the subject                          │
└──────────────────────────────────────────────────────────────────┘
             │
             ▼
         ( Finish )
```

FIG. 2B

RAINOUT PROTECTION FOR RESPIRATORY THERAPY INCLUDING HUMIDIFICATION

CROSS-REFERENCE TO PRIOR APPLICATIONS

This application is the U.S. National Phase application under 35 U.S.C. § 371 of International Application Serial No. PCT/IB2013/051399, filed on Feb. 21, 2013, which claims the benefit of U.S. application Ser. No. 61/602,638 filed on Feb. 24, 2012. These applications are hereby incorporated by reference herein.

BACKGROUND

1. Field

The present disclosure pertains to systems and methods for providing respiratory therapy of a subject. In particular, the present disclosure pertains to inhibiting condensation or rainout in respiratory therapy that includes humidification.

2. Description of the Related Art

It is well known that some types of respiratory therapy involve the delivery of a pressurized flow of breathable gas to the airway of a subject. It is known that a therapy session may (be intended to) span eight or more hours, and may (be intended to) coincide and/or overlap, at least in part, with a subject's daily and/or nightly sleeping period. It is known that a subject's comfort during a therapy session is a useful factor in therapy adoption rates and/or therapy success rates. It is known that a flow of breathable gas may be pressurized at varying levels of pressure, even during a single therapy session. It is known that humidification of the pressurized flow of breathable gas may improve a subject's comfort. It is known that heated humidification may improve a subject's comfort. It is known that condensation may form along the subject interface of respiratory therapy systems that include heated humidification. It is known that the formation of condensation, or rainout, has various downsides, including but not limited to reduced comfort of the subject.

It is known that algorithms may operate to control the humidity level and/or temperature used in respiratory therapy during a therapy session, for example using feedback. It is known that such algorithms may autonomously and/or automatically change operational settings of respiratory therapy systems to cause a particular effect, such as, by way of non-limiting example, maintaining a target level of relative humidity within the subject interface. Such algorithms may be based on various detections, conditions, settings, preferences, and/or occurrences of respiratory events. It is known that such algorithms may operate within a range of permitted levels, for example for the temperature of the delivered pressurized, humidified flow of breathable gas, including a minimum level and a maximum level that form the boundaries of such a range.

SUMMARY

Accordingly, it is an object of one or more embodiments of the present disclosure to provide a system configured to provide respiratory therapy to a subject. The system comprises: a pressure generator configured to generate a pressurized flow of breathable gas for delivery to an airway of a subject; a humidifier configured to controllably heat a liquid such that vapor formed from the heated liquid adds moisture to the pressurized flow of breathable gas; a subject interface configured to guide the humidified, pressurized flow of breathable gas to the airway of the subject; an interface heater configured to controllably heat the humidified, pressurized flow of breathable gas within the subject interface; one or more sensors configured to generate output signals conveying information related to one or more parameters of the humidified, pressurized flow of breathable gas within the subject interface; and one or more processors configured to execute processing modules.

The processing modules comprise: a target temperature module configured to obtain a target temperature for the humidified, pressurized flow of breathable gas within the subject interface; a target humidity module configured to obtain a target humidity for the humidified, pressurized flow of breathable gas within the subject interface; a temperature module configured to determine a current temperature of the humidified, pressurized flow of breathable gas based on the output signals; a heater control module configured to control the interface heater to maintain the current temperature of the humidified, pressurized flow of breathable gas within the subject interface at or above the target temperature, wherein the heater control module is further configured to control the interface heater such that the heat generated by the interface heater is adjusted to an amount not lower than a minimum amount of heat that is greater than zero; and a humidifier control module configured to control the humidifier to control a rate at which vapor is generated from the liquid to maintain the target humidity based on the current temperature, wherein, responsive to the current temperature being elevated by at least a minimum elevation level above the target temperature due to a heat influence of the subject, the humidifier control module is further configured to control the humidifier to control the rate at which the vapor is generated from the liquid as if the current temperature were equal to the target temperature, thereby inhibiting condensation from forming along the subject interface by the humidified, pressurized flow of breathable gas between the pressure generator and the airway of the subject.

It is yet another aspect of one or more embodiments of the present disclosure to provide a method for providing respiratory therapy to a subject. The method comprises: generating a pressurized flow for delivery to an airway of the subject during respiratory therapy, wherein the pressurized flow includes breathable gas; controllably heating a liquid such that vapor formed from the heated liquid adds moisture to the pressurized flow; guiding the humidified, pressurized flow to the airway of the subject via a subject interface; controllably heating the humidified, pressurized flow within the subject interface; generating one or more output signals conveying information related to one or more gas parameters of the humidified, pressurized flow; obtaining a target temperature for the humidified, pressurized flow within the subject interface; obtaining a target humidity for the humidified, pressurized flow within the subject interface; determining a current temperature of the humidified, pressurized flow within the subject interface based on the output signals; controlling the heating of the humidified, pressurized flow such that the current temperature is maintained at or above the target temperature, and further controlling the heating of the humidified, pressurized flow such that the heating is adjusted to an amount not lower than a minimum amount of heat that is greater than zero; detecting whether the current temperature is being elevated by at least a minimum elevation level above the target temperature due to a heat influence of the subject; and controlling the formation of vapor to maintain the target humidity based on the current temperature, wherein, responsive to the detection, the formation of vapor is further controlled to maintain the target humidity as if the current temperature were equal to the target temperature, thereby inhibiting condensation from forming along the subject interface by the humidified, pressurized flow of breathable gas between the pressure generator and the airway of the subject.

It is yet another aspect of one or more embodiments to provide a system configured to provide respiratory therapy to a subject. The system comprises: means for generating a pressurized flow for delivery to an airway of the subject during respiratory therapy, wherein the pressurized flow includes breathable gas; means for controllably heating a liquid such that vapor formed from the heated liquid adds moisture to the pressurized flow; interface means for guiding the humidified, pressurized flow to the airway of the subject; means for controllably heating the humidified, pressurized flow within the interface means; means for generating one or more output signals conveying information related to one or more gas parameters of the humidified, pressurized flow; means for obtaining a target temperature for the humidified, pressurized flow within the interface means; means for obtaining a target humidity for the humidified, pressurized flow within the interface means; means for determining a current temperature of the humidified, pressurized flow within the interface means based on the output signals; means for controlling the heating of the humidified, pressurized flow such that the current temperature is maintained at or above the target temperature by controllably applying heat, wherein the means for controlling the heating of the humidified, pressurized flow further controls the heating of the humidified, pressurized flow such that the heating is adjusted to an amount not lower than a minimum amount of heat that is greater than zero; means for detecting whether the current temperature is being elevated by at least a minimum elevation level above the target temperature due to a heat influence of the subject; and means for controlling the formation of vapor to maintain the target humidity based on the current temperature, wherein, responsive to the detection, the formation of vapor is further controlled to maintain the target humidity as if the current temperature were equal to the target temperature, thereby inhibiting condensation from forming along the subject interface by the humidified, pressurized flow of breathable gas between the pressure generator and the airway of the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIGS. 2A-2B illustrate a method for providing respiratory therapy to the airway of a subject that includes humidification, according to certain embodiments.

DETAILED DESCRIPTION OF EXEMPLARY EMBODIMENTS

Figure 1:
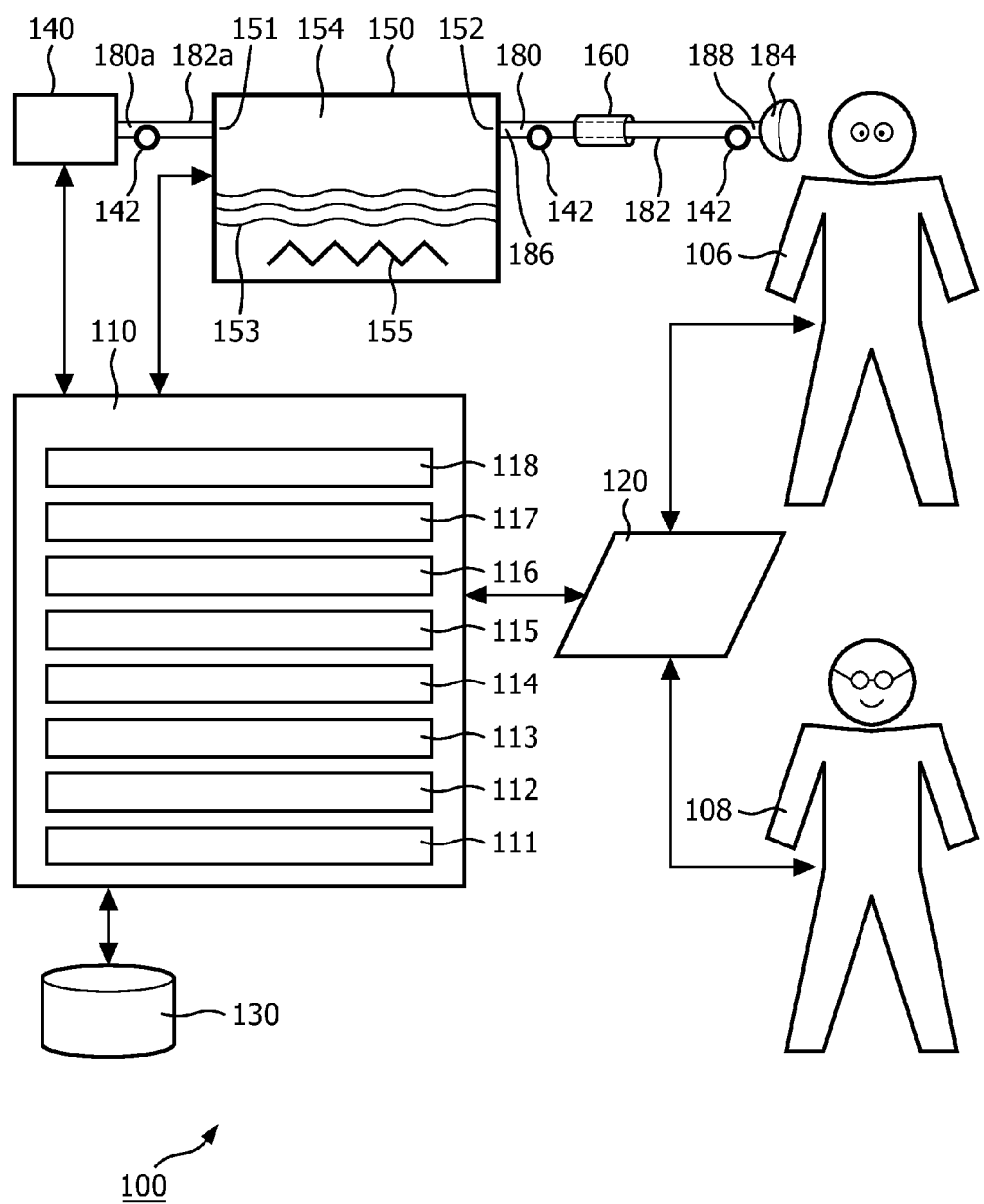
FIG. 1 schematically illustrates a system configured to provide respiratory therapy of a subject, according to certain embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 configured to provide respiratory therapy including humidification to the airway of a subject 106. System 100 may be implemented as, integrated with, and/or operating in conjunction with a respiratory device that provides a flow of breathable gas along a flow path to subject 106. Humidifying the flow of gas, e.g. by adding moisture in the form of water vapor, may improve the experience and/or comfort of subject 106. Humidification may be beneficial for other reasons than those stated herein, as commonly known in relevant fields of technology. The amount and/or level of moisture added, which may e.g. be expressed as a relative humidity percentage, may be monitored and/or controlled, e.g. through feedback, within the respiratory device.

System 100 may include one or more of a pressure generator 140, a humidifier 150, a subject interface 180, an interface heater 160, one or more sensors 142, an electronic storage 130, a user interface 120, a processor 110, a target temperature module 111, a target humidity module 112, a temperature module 113, a heater control module 114, a humidifier control module 115, an influence detection module 116, a control module 117, a parameter determination module 118, and/or other components. System 100 is configured to inhibit condensation from forming along a subject interface of system 100 before delivery of a humidified, pressurized flow of breathable gas to a subject.

Pressure generator 140 of system 100 in FIG. 1 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via one or more subject interfaces 180. Subject interface 180 may sometimes be referred to as a delivery circuit.

Pressure generator 140 may be integrated, combined, or connected with humidifier 150 in a configuration that is configured to humidify a flow of breathable gas within system 100. In the configuration depicted in FIG. 1, pressure generator 140 fluidly communicates with humidifier 150 via a subject interface 180a, which may be structurally and/or functionally similar to subject interface 180, at least in part. As depicted in FIG. 1, humidifier 150 fluidly communicates, via subject interface 180, with the airway of subject 106, after the flow of breathable gas passes interface heater 160. The configuration of various components in FIG. 1 is not intended to limit the scope of the described technology in any way. For example, in some embodiments, interface heater 160 may be disposed between pressure generator 140 and humidifier 150. In some embodiments, humidifier 150 may be disposed upstream from pressure generator 140. In some embodiments, interface heater 160 may be integrated in one or more other components of system 100.

Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Other schemes for providing respiratory support and/or ventilation through the delivery of the pressurized flow of breathable gas are contemplated. Subject 106 may or may not initiate one or more phases of respiration.

System 100 may be configured to adjust and/or maintain levels of pressure, flow, humidity, velocity, acceleration, and/or other parameters of the humidified, pressurized flow of breathable gas. One or more adjustments may occur in substantial synchronization with the breathing cycle of the subject. In some embodiments, one or more operating levels (e.g. pressure, volume, etc.) are adjusted on a relatively ongoing manner (e.g., each breath, every few breaths, every few seconds, etc.) during an individual session of respiratory therapy to titrate the therapy. Alternatively, and/or simultaneously, adjustments to one or more operating levels may be made more intermittently and/or between therapy sessions rather than during a particular therapy session.

A pressurized flow of breathable gas may be delivered from pressure generator 140 to the airway of subject 106 via one or more subject interfaces 180. Subject interface 180 may include a conduit 182 and/or a subject interface appliance 184. For example, as depicted in FIG. 1, subject interface 180a may include a conduit 182a. Subject interface 180 may include conduit 182. Conduit 182 and/or conduit 182a may include a flexible length of hose, or other conduit. As depicted in FIG. 1, conduit 182 may place subject interface appliance 184 in fluid communication with humidifier 150, and, indirectly, with pressure generator 140. As depicted in FIG. 1, subject interface 180 may include a proximal end 186 disposed at or near humidifier 150 and a distal end 188 disposed at or near subject interface appliance 184. Conduit 182 and/or conduit 182a form a flow path through which the pressurized flow of breathable gas is communicated between subject interface appliance 184, humidifier 150, and pressure generator 140.

Subject interface appliance 184 of system 100 in FIG. 1 is configured to deliver the pressurized flow of breathable gas to the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface. In some embodiments, interface heater 160 may be embedded and/or integrated within subject interface appliance 184.

Interface heater 160 of system 100 in FIG. 1 is configured to controllably heat a flow of breathable gas within system 100, particularly within subject interface 180 and/or subject interface 180a. As depicted in FIG. 1, interface heater 160 is configured to heat the humidified, pressurized flow of breathable gas within subject interface 180 en route to the airway of subject 106. The depiction of interface heater 160 as a single component is not intended to be limiting in any way. The depiction of interface heater 160 as operating on a segment or portion of conduit 182 is not intended to be limiting in any way.

Interface heater 160 may be implemented as a heated coil wrapped around and/or embedded within conduit 182 and/or other components of interface 180. Other ways to add heat to system 100 are contemplated, as commonly known in relevant fields of technology. Thermal exchange through interface heater 160 is not limited to an embodiment using one or more heated coils. In some embodiments, interface heater 160 may be embedded and/or integrated within another component of system 100.

Humidifier 150 is configured to controllably humidify the flow of breathable gas in system 100. In some embodiments, humidifier 150 is configured to controllably heat a liquid such that vapor formed from the heated liquid adds moisture to a flow of breathable gas. Humidifier 150 may include one or more of a gas inlet 151, a gas outlet 152, a humidification chamber 154 configured to contain liquid, liquid 153 intended to be vaporized, a heating element 155, and/or other components. A flow of breathable gas may be received through gas inlet 151. The flow of breathable gas may be humidified within humidification chamber 154 by liquid vapor formed from liquid 153 being heated. Liquid 153 may be heated through heating element 155. The humidified flow of breathable gas may be released from humidification chamber 154 and/or humidifier 150 through gas outlet 152. In some embodiments, heating element 155 may be disposed at or near the bottom of humidification chamber 154 and/or in proximity to liquid 153 within humidification chamber 154. In some embodiments, heating element 155 may not come in direct contact with liquid 153. The heat emitted by heating element 155 may be dispensed into liquid 153, e.g. indirectly, and vaporize liquid 153.

As depicted in FIG. 1, gas inlet 151 may fluidly communicate with subject interface 180a to receive a flow of pressurized breathable gas from pressure generator 140, disposed upstream. As depicted in FIG. 1, gas outlet 152 may fluidly communicate with subject interface 180 to guide the humidified, pressurized flow of breathable gas from humidifier 150 to the airway of subject 106 via subject interface appliance 184. Humidifier 150, as depicted in FIG. 1 is disposed downstream from subject interface appliance 184. In some embodiments, the humidified, pressurized flow of breathable gas may include medicament. In some embodiments, interface heater 160 may be embedded and/or integrated within humidifier 150, for example at or near gas outlet 152 and/or proximal end 186 of subject interface 180.

Humidity of air or other breathable gases is known to vary with temperature. As a consequence, a temperature differential, e.g. along subject interface 180, may affect the relative humidity within subject interface 180. In particular, a temperature differential along a subject interface may cause condensation. By way of illustration, the following chart illustrates relative humidity levels ranging from 85% to 95%, and, corresponding thereto, absolute humidity levels in mg/l. for a humidified flow of gas at a temperature of 78° F.:

| Humidity at 78° F. | | | | | | | | | | |
|---|---|---|---|---|---|---|---|---|---|---|
| 85% | 86% | 87% | 88% | 89% | 90% | 91% | 92% | 93% | 94% | 95% |
| 20.14 | 20.38 | 20.61 | 20.85 | 21.09 | 21.33 | 21.56 | 21.80 | 22.04 | 22.27 | 22.51 |

By way of further illustration, the absolute humidity at which condensation or rainout occurs, i.e. 100% relative humidity, is illustrated in the following chart for temperatures ranging from 68° F. to 78° F. Note that degrees Fahrenheit may interchangeably be annotated with ° F. or F herein. Note that degrees Celsius may interchangeably be annotated with ° C. or C herein.

| Absolute humidity at which condensation occurs for temperatures ranging from 68 F. to 78 F. | | | | | | | | | | |
|---|---|---|---|---|---|---|---|---|---|---|
| 68 F. | 69 F. | 70 F. | 71 F. | 72 F. | 73 F. | 74 F. | 75 F. | 76 F. | 77 F. | 78 F. |
| 17.24 | 17.81 | 18.39 | 19.00 | 19.61 | 20.25 | 20.90 | 21.57 | 22.26 | 22.97 | 23.70 |

For example, assume the target temperature within a subject interface of a respiratory device is 78 F, and the target relative humidity is 85%. Such targets may be interchangeably referred to herein as a temperature set point and/or (relative) humidity set point. According to the first chart, the absolute humidity corresponding to the given set points in this example is 20.14 mg/l. If a section or location of the subject interface has a temperature below 73 F, condensation or rainout may occur at that location.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas and/or respiratory parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing occurrences of respiratory events throughout a period during which the subject is receiving therapy. An example of information that user 108 or subject 106 may provide to system 100 is a target temperature or target humidity level during respiratory therapy. Examples of interface devices suitable for inclusion in user interface 120 include a keypad, buttons, switches, a keyboard, knobs, dials, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the embodiment of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying measurements related to parameters of the flow of breathable gas within system 100. These parameters may include one or more of flow, (airway) pressure, barometric pressure, humidity, velocity, acceleration, and/or other parameters. One or more sensors 142 may be in fluid communication with conduit 182a, conduit 182, subject interface appliance 184, and/or other components of system 100. One or more sensors 142 may generate output signals related to physiological parameters pertaining to subject 106.

One or more sensors 142 may generate output signals conveying information related to parameters associated with the state and/or condition of an airway of subject 106, the breathing of subject 106, the breathing rate of subject 106, the gas delivered to subject 106, the composition and/or humidity of the gas delivered to subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from one or more sensors 142 may be transmitted to processor 110, user interface 120, electronic storage 130, and/or other components of system 100. This transmission may be wired and/or wireless.

The illustration of sensor 142 including three members in FIG. 1 is not intended to be limiting. The illustration of a sensor 142 at or near subject interface appliance 184 is not intended to be limiting, though that location may be preferred in some embodiments to provide feedback and/or information regarding the current temperature of the humidified, pressurized flow of breathable gas being delivered to the airway of subject 106. For example, this current temperature may function as feedback for a target temperature or set point for controlling interface heater 160. Note that a temperature differential may occur along subject interface 180.

The illustration of a sensor 142 at or near gas outlet 152 of humidifier 150 in FIG. 1 is not intended to be limiting, though that location may be preferred in some embodiments to provide feedback and/or information regarding the current relative humidity percentage of the flow of breathable gas being released from humidifier 150. For example, this current relative humidity percentage may function as feedback for a target relative humidity percentage or set point for controlling humidifier 150 and/or heating element 155. Note that the relative humidity percentage within subject interface 180 may depend on localized temperatures along subject interface 180. For example, a temperature differential within subject interface 180 may cause condensation to occur locally, at one or more locations, within subject interface 180.

The illustration of a sensor 142 at or near pressure generator 140 in FIG. 1 is not intended to be limiting, though that location may be preferred in some embodiments to provide feedback and/or information regarding the current pressure level of the flow of breathable gas being provided by pressure generator 140.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of target temperature module 111, target humidity module 112, temperature module 113, heater control module 114, humidifier control module 115, influence detection module 116, control module 117, parameter determination module 118, and/or other modules. Processor 110 may be configured to execute modules 111-118 by software; hardware; firmware; some combination of software, hardware, and/or firmware; and/or other mechanisms for configuring processing capabilities on processor 110.

It should be appreciated that although modules 111-118 are illustrated in FIG. 1 as being co-located within a single processing unit, in embodiments in which processor 110 includes multiple processing units, one or more of modules 111-118 may be located remotely from the other modules. The description of the functionality provided by the different modules 111-118 described herein is for illustrative purposes, and is not intended to be limiting, as any of modules 111-118 may provide more or less functionality than is described. For example, one or more of modules 111-118 may be eliminated, and some or all of its functionality may be provided by other ones of modules 111-118. Note that processor 110 may be configured to execute one or more additional modules that may perform some or all of the functionality attributed below to one of modules 111-118. In some embodiments, some or all of the described functionality of an individual computer program module may be incorporated, shared, embedded, and/or integrated into one or more other computer program modules or elsewhere within system 100.

Control module 117 is configured to control pressure generator 140 to adjust one or more gas parameters, describes elsewhere herein, of the pressurized flow of breathable gas in accordance with a respiratory therapy regimen, one or more algorithms that control adjustments and/or changes in the pressurized flow of breathable gas over time, operational settings, and/or other factors. For example, subject 106 or user 108 may provide one or more settings that correspond to one or more particular pressure levels, one or more modes of operation, and/or one or more preferences related to the operation of pressure generator 140. The control module may be configured to control pressure generator 140 to provide the pressurized flow of breathable gas. The control module may be configured to control pressure generator 140 such that one or more gas parameters of the pressurized flow of breathable gas are varied over time in accordance with a respiratory therapy regimen. The control module may be configured to control pressure generator 140 to provide the pressurized flow of breathable gas at inhalation pressure levels during inhalation phases, and/or at exhalation pressure levels during exhalation phases.

Parameters determined by other modules of system 100 and/or received through sensors 142 can be used by the control module, e.g. in a feedback manner, to adjust one or more therapy modes/settings/operations of system 100. Alternatively, and/or simultaneously, signals and/or information received through user interface 120 may be used by the control module to adjust one or more therapy modes/settings/operations of system 100. The control module may be configured to time its operations relative to transitional moments in the breathing cycle of a subject, over multiple breath cycles, and/or in any other relation to, e.g., any determinations by any of the computer program modules of system 100.

Parameter determination module 118 is configured to determine one or more gas parameters, breathing parameters, and/or other parameters from output signals generated by sensor(s) 142. The one or more gas parameter may include and/or be related to one or more of (peak) flow, flow rate, (tidal) volume, pressure, temperature, humidity, velocity, acceleration, gas composition (e.g. concentration(s) of one or more constituents such as, e.g., water vapor or $CO_2$), thermal energy dissipated, and/or other measurements related to the pressurized flow of breathable gas. For example, one or more of these gas parameters, such as pressure and/or volume, may be used by the control module, described above, during respiratory therapy.

One or more breathing parameters may be derived, e.g. by parameter determination module 118, from gas parameters and/or from sensor-generated output signals conveying measurements of e.g., the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters. Some or all of this functionality may be incorporated, shared, and/or integrated into other computer program modules of processor 110.

Target temperature module 111 is configured to obtain a target temperature for the flow of breathable gas. For example, the target temperature may pertain to the temperature of the humidified, pressurized flow of breathable gas within subject interface 180. In some embodiments, subject 106 and/or user 108 may provide and/or select the target temperature, for example through user interface 120. For example, subject 106 may adjust the target temperature based on personal preference. In some embodiments, subject 106 may select a preferred offset temperature as the target temperature, wherein the offset temperature is based on and/or relative to the current ambient temperature. Alternatively, and/or simultaneously, the target temperature may be derived and/or determined based on one or more other selectable and/or adjustable operational settings.

Target humidity module 112 is configured to obtain a target humidity for a flow of breathable gas. For example, the target humidity may pertain to the humidified, pressurized flow of breathable gas within subject interface 180. The target humidity level may be an absolute humidity level, a relative humidity percentage, and/or a combination of both. In some embodiments, subject 106 and/or user 108 may provide and/or select the target humidity, for example through user interface 120. For example, subject 106 may adjust the target humidity based on personal preference. In some embodiments, subject 106 may select a preferred offset humidity as the target humidity, wherein the offset humidity is based on and/or relative to the current ambient humidity or the current humidity within subject interface 180. Alternatively, and/or simultaneously, the target humidity may be derived and/or determined based on one or more other selectable and/or adjustable operational settings. For example, a change in target humidity may be based on a change in the current temperature within subject interface 180, a change in the current amount of heat influence due to subject 106 (as described elsewhere herein), and/or be based on one or more other operational and/or environmental conditions during use of system 100.

Temperature module 113 is configured to determine a current temperature of a flow of breathable gas. For example, the current temperature may pertain to the temperature of the humidified, pressurized flow of breathable gas within subject interface 180. The current temperature may be determined based on one or more output signals generated by one or more sensors 142. For example, the current temperature within subject interface 180 may be determined based on a sensor 142 at or near subject interface appliance 184, as illustrated in FIG. 1. In some embodiments, temperature module 113 may be implemented as part of a parameter determination module, for example the parameter determination module described above.

System 100 may include an influence detection module 116 configured to detect whether the current temperature, as determined by temperature module 113, within subject interface 180 is being elevated, due to a heat influence of subject 106, above a threshold temperature (e.g., elevated by at least a minimum elevation level above the target temperature obtained by target temperature module 111). The heat influence may be caused by the respiration of subject 106. The heat influence may be quantified using one or more gas and/or breathing parameters, or a combination thereof. For example, the heat influence may be based on and/or quantified using a combination of breathing rate, tidal volume, current temperature at or near subject interface appliance 184, and/or other parameters.

The minimum elevation level may be a predetermined absolute temperature elevation compared to the target temperature. For example, the minimum elevation level may be 1° F., 2° F., 2.5° F., 3° F., 3.5° F., 4° F., 5° F., 6° F., and/or another number of degrees Fahrenheit. In some embodiments, the minimum elevation level may be 1° C., 1.5° C., 2° C., 2.5° C., 3° C., 3.5° C., 4° C. and/or another number of degrees Celsius. Alternatively, and/or simultaneously, the minimum elevation level may be a predetermined temperature offset relative to the current ambient temperature. For example, the temperature offset may be 1° F., 2° F., 2.5° F., 3° F., 3.5° F., 4° F., 5° F., 6° F., and/or another number of degrees Fahrenheit. In some embodiments, the temperature offset may be 1° C., 1.5° C., 2° C., 2.5° C., 3° C., 3.5° C., 4° C. and/or another number of degrees Celsius.

The minimum elevation level may be dependent on and/or specific to the type of components used in system 100. For example, the minimum elevation level may be different for different types of subject interface appliance 184 that may be used during respiratory therapy. For example, some masks allow a tighter seal, which may more easily or commonly cause a heat influence at or above the minimum elevation level to be exerted by subject 106. In some embodiments, the minimum elevation level may be dependent on one or more locations of one or more sensors 142. In some embodiments, the minimum elevation level may be dependent on operating and/or environmental parameters, including but not limited to flow rate, ambient temperature, and/or other parameters.

Responsive to a detection as described, e.g. by influence detection module 116, of an elevated temperature within subject interface 180, one or more constituent components of system 100 may respond, adapt, and/or change operation in order to prevent condensation or rainout within system 100.

Heater control module 114 is configured to control interface heater 160 to maintain the current temperature of the humidified, pressurized flow of breathable gas within the subject interface 180 at or above the target temperature. The current temperature within subject interface 180 may be determined by temperature module 113. Heater control module 114 may use the current temperature as feedback to control interface heater 160.

Heater control module 114 may be further configured, for example once the target temperature has been reached during a particular therapy session, to control interface heater 160 such that at least a minimum amount of heat is generated and applied to the humidified, pressurized flow of breathable gas within subject interface 180, despite the current temperature being elevated above the target temperature. Generated and applied heat may be simply referred to herein as energy. For example, if the current temperature at or near distal end 188 of subject interface 180 is elevated, due to a heat influence by subject 106, the generated and applied level of heat or energy, as controlled by heater control module 114, may be an amount no lower than the minimum amount of heat or energy. As described elsewhere, a temperature differential within subject interface 180 may cause condensation to occur. By applying at least the minimum amount of heat despite the current temperature being elevated above the target temperature at or near subject interface appliance 184 due to subject influence, the local temperature within subject interface 180 between subject interface appliance 184 and humidifier 150 is maintained at a high enough temperature to significantly reduce the risk of condensation through this portion of subject interface 180. The minimum amount of heat is greater than zero.

In some embodiments, the minimum amount of heat may be an absolute amount or offset amount of heat similar to and/or sufficient to elevate the described local temperature by a predetermined number of degrees. The predetermined absolute amount or offset number of degrees used as basis for the minimum amount of heat applied by heater control module 114 may be 1° F., 2° F., 2.5° F., 3° F., 3.5° F., 4° F., 5° F., 6° F., and/or another number of degrees Fahrenheit, or it may be 1° C., 1.5° C., 2° C., 2.5° C., 3° C., 3.5° C., 4° C. and/or another number of degrees Celsius.

Alternatively, and/or simultaneously, the minimum amount of heat may be relative to and/or based on the current temperature, the target temperature, the ambient temperature, and/or any combination thereof. For example, the minimum amount of heat generated may correspond to an amount of heat sufficient to elevate the temperature of the humidified, pressurized flow of breathable gas by about 1° F., 2° F., 2.5° F., 3° F., 3.5° F., 4° F., 5° F., 6° F., and/or another number of degrees Fahrenheit, or by about 1° C., 1.5° C., 2° C., 2.5° C., 3° C., 3.5° C., 4° C., and/or another number of degrees Celsius relative to an ambient temperature within standard operating ranges of ambient temperature between about 32° F. and 120° F. In some embodiments, the relative minimum amount of heat may be determined as a percentage of the current temperature, the target temperature, the ambient temperature, and/or any combination thereof.

Humidifier control module 115 is configured to control humidifier 150 to control a rate at which vapor is generated to maintain the target humidity based on the current temperature, e.g. from temperature module 113. In some embodiments, control of humidifier 150 includes control of heater element 155. In some embodiments, the rate at which vapor is generated may be measured, determined, estimated, and/or approximated based on a measurement of the current humidity within subject interface 180 and/or at or near gas outlet 152. For example, a sensor 142 disposed at or near gas outlet 152 may generate one or more output signals conveying information related to the current relative humidity percentage of the flow of pressurized breathable gas as released by humidifier 150. This current humidity percentage may be used as feedback to control heater element 155 of humidifier 150.

Responsive to a detection by system 100 of a particular heat influence due to subject 106, humidifier control module 115 may be configured to control humidifier 150 to control a rate at which vapor is generated to maintain the target humidity for a temperature that is lower than the current temperature. By maintaining the same relative humidity percentage for a lower feedback temperature, the actual relative humidity of the pressurized flow of breathable gas at the higher temperature near subject 106 is lower than the target humidity. In some embodiments, responsive to a detection as described above, the target humidity is maintained for the target temperature even though the influence from subject 106 has elevated the temperature within at least a portion of subject interface 184 above the target temperature. In some embodiments, responsive to a detection as described above, the target humidity is maintained for a temperature that is lower than the current temperature by a predetermined amount of degrees. In some embodiments, responsive to a detection as described above, the target humidity is maintained for a temperature that is lower than the current temperature by a predetermined relative amount or percentage. In some embodiments, responsive to a detection as described above, the target humidity is maintained for a temperature that is based on an ambient temperature. It is contemplated that one or more embodiments may be combined. For example, responsive to a detection as described above, the target humidity may be is maintained for a temperature that is based on a percentage of the difference between the current temperature and the target temperature.

Responsive to a detection as described above, applying additional heat, through interface heater 160, thus accomplishes one or more of reducing the temperature differential, reducing the actual relative humidity by maintaining the target humidity for a lower temperature, and/or other adjustments, thus inhibiting condensation from forming along subject interface 180.

Figure 3A:
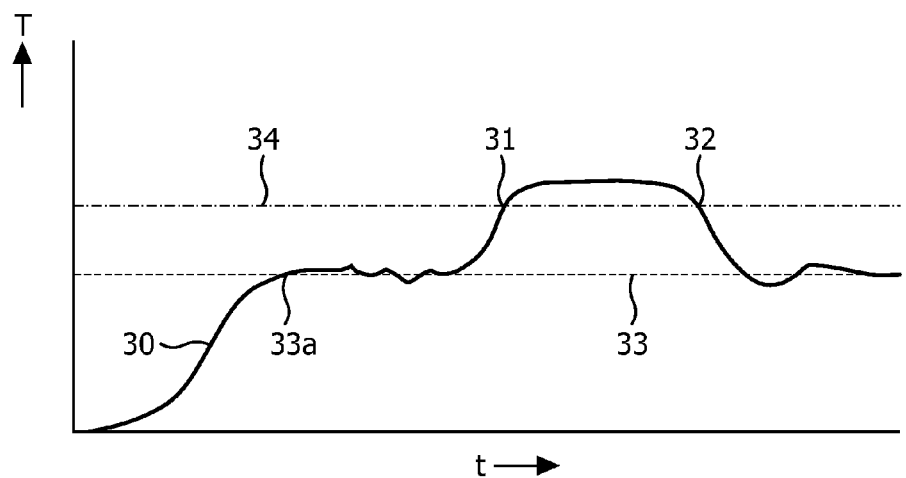
FIGS. 3A-3B illustrates graphs depicting changes over time for the current temperature (FIG. 3A) and amount of energy applied (FIG. 3B) in a system according to one or more embodiments.

By way of illustration, FIG. 3A illustrates a graph 30 depicting the current temperature of the humidified, pressurized flow of gas over time. Target temperature 33 remains constant in graph 30. Minimum elevation level 34 depicts a constant temperature offset based on target temperature 33. Minimum elevation level 34 is used for detection of a particular heat influence by a subject. At the start of graph 30, the current temperature gradually increases until target temperature 33 is reached at point 33a. Once target temperature 33 is reached, the current temperature is fairly constant. The current temperature may go up and down slightly as a heater control module controls an interface heater, for example by using the current temperature as feedback information, to maintain the current temperature at target temperature 33, but the changes in the current temperature are not sufficient to reach minimum elevation level 34. The current temperature remains fairly constant until the sudden elevation of the current temperature that culminates, at a point 31 of graph 30, in the current temperature breaching minimum elevation level 34 above target temperature 33. At this point, the likelihood of condensation within a subject interface due to temperature differential increases. In response to the detection of the circumstances at point 31, a humidifier control module may control the rate at which vapor is generated to maintain the target humidity for target temperature 33, rather than based on the current temperature. This reduces the actual relative humidity level.

Again, the current temperature remains fairly constant until the sudden drop of the current temperature at or near point 32. At point 32, the current temperature ceases to breach minimum elevation level 34. In response to the detection of the circumstances at point 32, a humidifier control module may control the rate at which vapor is generated to maintain the target humidity for the current temperature, rather than based on target temperature 33.

Figure 3B:
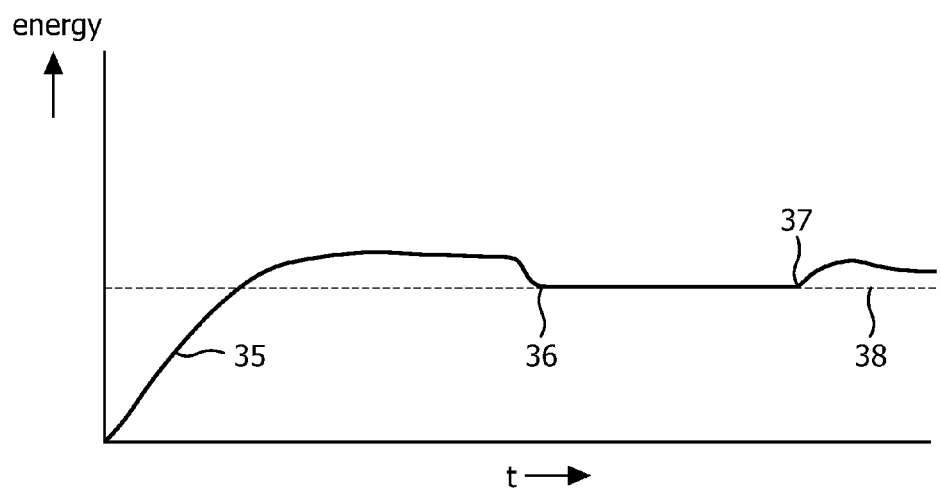

By way of illustration, FIG. 3B illustrates a graph 35 depicting a current amount of heat or energy generated and applied to the humidified, pressurized flow of gas over time. Minimum amount 38 of heat or energy generated and applied to the humidified, pressurized flow of breathable gas within a subject interface remains constant in graph 35. Minimum amount 38 may be used by a heat control module. At the start of graph 35, the current amount of heat increases, roughly until the target temperature is reached. Once the target temperature is reached, the current amount of heat remains fairly constant until the sudden decrease in the current amount of heat at or near point 36. This sudden decrease may correspond to a sudden increase in the current temperature, for example above a minimum elevation level. The current amount of heat remains fairly constant at an amount no lower than minimum amount of heat 38, despite the current temperature being elevated above the target temperature. The current amount of energy remains fairly constant until a drop in the current temperature, for example below a minimum elevation level or a target temperature, at or near point 37. In response to the drop in the current temperature, the current amount of heat may for example be increased, after point 37, to maintain the current temperature at the target temperature.

Referring to FIG. 1, and by further way of illustration, the following chart illustrates the absolute humidity levels corresponding to relative humidity percentages for a current (feedback) temperature of 72° F.:

| Relative and absolute humidity at a current temperature of 72° F. | | | | | | | | | | |
|---|---|---|---|---|---|---|---|---|---|---|
| 85 | 86 | 87 | 88 | 89 | 90 | 91 | 92 | 93 | 94 | 95 |
| 16.67 | 16.87 | 17.06 | 17.26 | 17.46 | 17.65 | 17.85 | 18.04 | 18.24 | 18.44 | 18.63 |

For example, assume that a current temperature at or near subject interface appliance 184 is 72 F, for example in part due to a heat influence. Assume a target relative humidity of 95%. Assume that the current ambient temperature is 68 F. According to the preceding chart, the absolute humidity within subject interface 180 corresponding to the given set points in this example is 18.63 mg/l. If a section or location of subject interface 180 locally has a temperature below 71 F, e.g. in a case whether the target temperature is 70 F, then the relative humidity at one or more locations within subject interface 180 may exceed 100%, causing condensation. System 100 may detect the heat influence in the preceding example and respond as described herein. Assume, for this example, that the minimum amount of heat applied by interface heater 160 under control of heater control module 114 corresponds to an amount of heat sufficient to elevate the temperature of the pressurized flow of breathable gas by three degrees above the ambient temperature. As a result, the absolute humidity of 18.63 mg/l in this example is below the minimum absolute humidity at which condensation can occur within subject interface 180 of 19.0 mg/l, which corresponds to a local temperature of 71 F within subject interface 180. Within standard operating conditions, condensation is inhibited for relative humidity percentages at or below 95% as illustrated by the preceding chart.

Figure 2A:
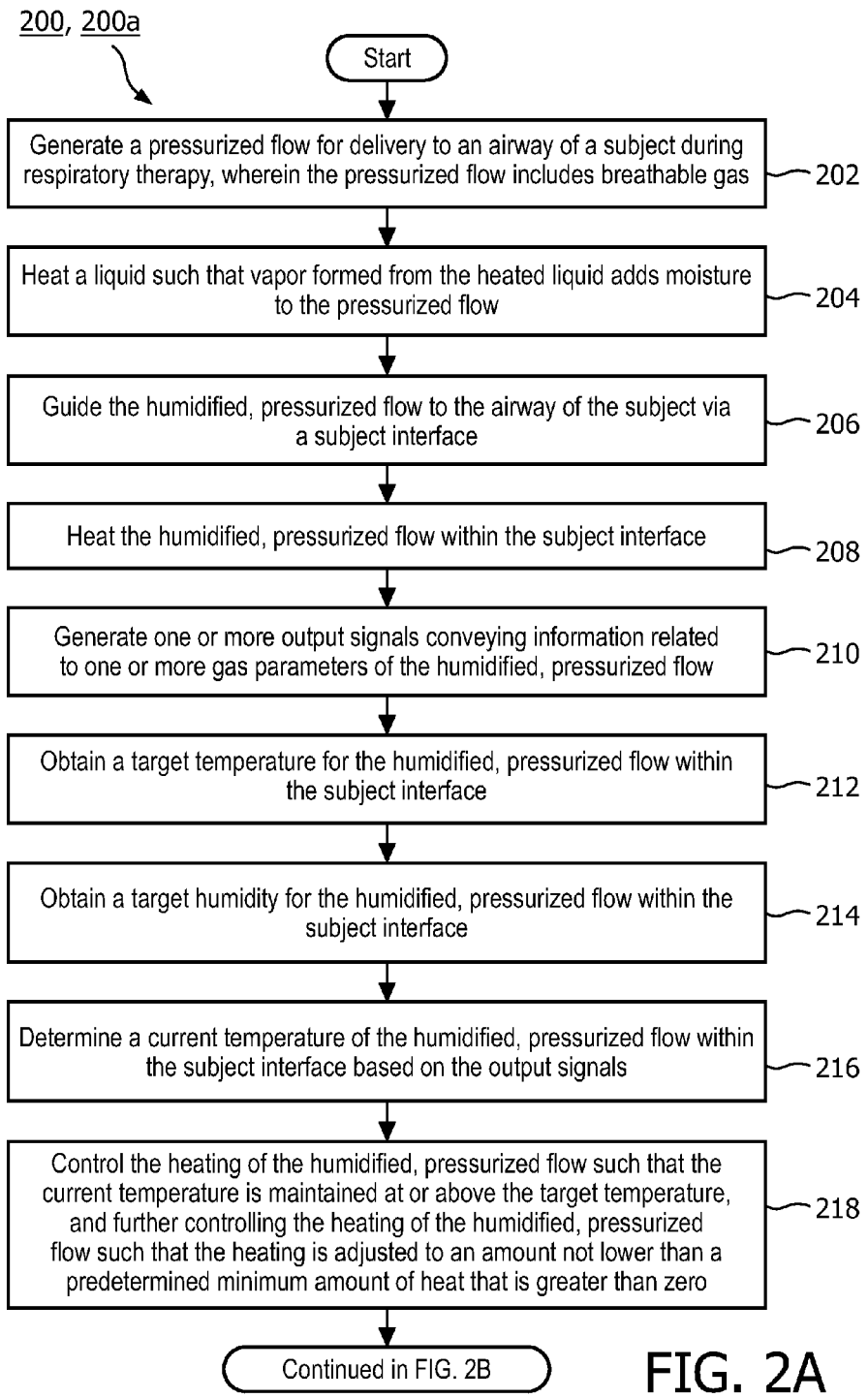

FIGS. 2A-2B illustrate a method 200 (comprising method segments 200a and 200b as depicted in FIG. 2A and FIG. 2B respectively) for providing respiratory therapy of a subject and inhibiting condensation from forming along a subject interface. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIGS. 2A-2B and described below is not intended to be limiting.

In certain embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is generated for delivery to an airway of a subject during respiratory therapy. In one embodiment, operation 202 is performed by a pressure generator similar to or substantially the same as pressure generator 140 (shown in FIG. 1 and described above).

At an operation 204, a liquid is heated such that vapor is formed from the heated liquid. The vapor adds moisture to the pressurized flow. In one embodiment, operation 204 is performed by a humidifier similar to or substantially the same as humidifier 150 (shown in FIG. 1 and described above).

At an operation 206, the humidified, pressurized flow of breathable gas is guided to the airway of the subject. In one embodiment, operation 206 is performed by a subject interface similar to or substantially the same as subject interface 180 (shown in FIG. 1 and described above).

At an operation 208, the humidified, pressurized flow of breathable gas is heated within the subject interface. In one embodiment, operation 208 is performed by an interface heater similar to or substantially the same as interface heater 160 (shown in FIG. 1 and described above).

At an operation 210, one or more output signals are generated that convey information related to one or more gas parameters of the humidified, pressurized flow of breathable gas. In one embodiment, operation 210 is performed by one or more sensors similar to or substantially the same as one or more sensors 142 (shown in FIG. 1 and described above).

At an operation 212, a target temperature is obtained for the humidified, pressurized flow of breathable gas within the subject interface. In one embodiment, operation 212 is performed by a target temperature module similar to or substantially the same as target temperature module 111 (shown in FIG. 1 and described above).

At an operation 214, a target humidity is obtained for the humidified, pressurized flow of breathable gas within the subject interface. In one embodiment, operation 214 is performed using a target humidity module similar to or substantially the same as target humidity module 112 (shown in FIG. 1 and described above).

At an operation 216, a current temperature is determined for the humidified, pressurized flow of breathable gas within the subject interface, based on one or more output signals. In one embodiment, operation 216 is performed by a temperature module similar to or substantially the same as temperature module 113 (shown in FIG. 1 and described above).

At an operation 218, heating of the humidified, pressurized flow of breathable gas is controlled such that the current temperature is maintained at or above the target temperature. Heating is further controlled such that the amount of heating is adjusted to an amount not lower than a predetermined minimum amount of heat that is greater than zero. In one embodiment, operation 218 is performed by a heater control module similar to or substantially the same as heater control module 114 (shown in FIG. 1 and described above).

At an operation 220, an elevation of the current temperature by at least a minimum elevation level above the target temperature due to a heat influence of the subject is detected. In one embodiment, operation 220 is performed by an influence detection module similar to or substantially the same as influence detection module 116 (shown in FIG. 1 and described above).

At an operation 222, the formation of vapor is controlled to maintain the target humidity based on the current temperature. Responsive to the detection of operation 220, the formation of vapor is controlled to maintain the target humidity as if the current temperature were equal to the target temperature, thereby inhibiting condensation from forming along the subject interface. In one embodiment, operation 222 is performed by a humidifier control module similar to or substantially the same as humidifier control module 115 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to provide respiratory therapy to a subject, the system comprising:
   a pressure generator configured to generate a pressurized flow of breathable gas for delivery to an airway of a subject;
   a humidifier configured to controllably heat a liquid such that vapor formed from the heated liquid adds moisture to the pressurized flow of breathable gas;
   a subject interface configured to guide the humidified, pressurized flow of breathable gas to the airway of the subject;
   an interface heater configured to controllably heat the humidified, pressurized flow of breathable gas within the subject interface;
   one or more sensors configured to generate output signals conveying information related to one or more parameters of the humidified, pressurized flow of breathable gas within the subject interface; and
   one or more processors configured to execute processing modules, the processing modules comprising:
      a target temperature module configured to obtain a target temperature for the humidified, pressurized flow of breathable gas within the subject interface;
      a target humidity module configured to obtain a target humidity for the humidified, pressurized flow of breathable gas within the subject interface;
      a temperature module configured to determine a current temperature of the humidified, pressurized flow of breathable gas based on the output signals;
      a heater control module configured to control the interface heater to maintain the current temperature of the humidified, pressurized flow of breathable gas within the subject interface at or above the target temperature, wherein the heater control module is further configured to control the interface heater such that the heat generated by the interface heater is adjusted to an amount not lower than a minimum amount of heat that is greater than zero;
      a humidifier control module configured to control the humidifier to control a rate at which vapor is generated from the liquid to maintain the target humidity based on the current temperature; and
      an influence detection module configured to detect whether the current temperature within the subject interface is elevated by at least a minimum elevation level above the target temperature due to a heat influence of the subject,
      wherein, responsive to the current temperature being elevated by at least the minimum elevation level above the target temperature due to the heat influence of the subject, the humidifier control module is further configured to control the humidifier to control the rate at which the vapor is generated from the liquid as if the current temperature were equal to the target temperature, thereby inhibiting condensation from forming along the subject interface by the humidified, pressurized flow of breathable gas between the pressure generator and the airway of the subject.

2. The system of claim 1, wherein the target humidity is a target relative humidity percentage.

3. The system of claim 1, wherein the minimum amount of heat generated by the interface heater under control of the heater control module corresponds to an amount of heat sufficient to elevate the temperature of the humidified, pressurized flow of breathable gas by about three degrees Fahrenheit relative to an ambient temperature within standard operating ranges.

4. The system of claim 1, wherein, responsive to the current temperature no longer being elevated by at least the minimum elevation level above the target temperature due to the heat influence of the subject, operation of the humidifier control module reverts to maintaining the target humidity based on the current temperature.

5. The system of claim 1, wherein operation of the humidifier control module is further based on a detection of the subject being actively engaged with the system, wherein the detection is based on one or more output signals.

6. The system of claim 1, wherein the influence detection module is configured to determine the minimum elevation level based on one or more of a type of subject interface appliance, a location of one of the one or more sensors, a flow rate of the pressurized flow of breathable gas, or an ambient temperature.

7. A method for providing respiratory therapy to a subject, the method comprising;
generating a pressurized flow for delivery to an airway of the subject during respiratory therapy, wherein the pressurized flow includes breathable gas;
controllably heating a liquid such that vapor formed from the heated liquid adds moisture to the pressurized flow;
guiding the humidified, pressurized flow to the airway of the subject via a subject interface;
controllably heating the humidified, pressurized flow within the subject interface;
generating one or more output signals conveying information related to one or more gas parameters of the humidified, pressurized flow;
obtaining a target temperature for the humidified, pressurized flow within the subject interface;
obtaining a target humidity for the humidified, pressurized flow within the subject interface;
determining a current temperature of the humidified, pressurized flow within the subject interface based on the output signals;
controlling the heating of the humidified, pressurized flow such that the current temperature is maintained at or above the target temperature, and further controlling the heating of the humidified, pressurized flow such that the heating is adjusted to an amount not lower than a minimum amount of heat that is greater than zero;
detecting whether the current temperature within the subject interface is elevated by at least a minimum elevation level above the target temperature due to a heat influence of the subject; and
controlling the formation of vapor to maintain the target humidity based on the current temperature, wherein, responsive to the current temperature within the subject interface being elevated by at least the minimum elevation level above the target temperature due to the heat influence of the subject, the formation of vapor is further controlled to maintain the target humidity as if the current temperature were equal to the target temperature, thereby inhibiting condensation from forming along the subject interface by the humidified, pressurized flow of breathable gas between the pressure generator and the airway of the subject.

8. The method of claim 7, wherein the target humidity is a target relative humidity percentage.

9. The method of claim 7, wherein the minimum amount of heat generated to heat the humidified, pressurized flow of breathable gas is based on an ambient temperature.

10. The method of claim 7, wherein, responsive to the current temperature no longer being elevated by at least the minimum elevation level above the target temperature due to the heat influence of the subject, controlling the formation of vapor to maintain the target humidity reverts to being based on the current temperature.

11. The method of claim 10, wherein controlling the formation of vapor to maintain the target humidity is further based on a detection of the subject being actively engaged with the subject interface, wherein the detection is based on one or more output signals.

12. The method of claim 7, further comprising determining the minimum elevation level based on one or more of a type of subject interface appliance, a location of one of the one or more sensors, a flow rate of the pressurized flow of breathable gas, or an ambient temperature.

13. A system configured to provide respiratory therapy to a subject, the system comprising;
means for generating a pressurized flow for delivery to an airway of the subject during respiratory therapy, wherein the pressurized flow includes breathable gas;
means for controllably heating a liquid such that vapor formed from the heated liquid adds moisture to the pressurized flow;
interface means for guiding the humidified, pressurized flow to the airway of the subject;
means for controllably heating the humidified, pressurized flow within the interface means;
means for generating one or more output signals conveying information related to one or more gas parameters of the humidified, pressurized flow;
means for obtaining a target temperature for the humidified, pressurized flow within the interface means;
means for obtaining a target humidity for the humidified, pressurized flow within the interface means;
means for determining a current temperature of the humidified, pressurized flow within the interface means based on the output signals;
means for controlling the heating of the humidified, pressurized flow such that the current temperature is maintained at or above the target temperature by controllably applying heat, wherein the means for controlling the heating of the humidified, pressurized flow further controls the heating of the humidified, pressurized flow such that the heating is adjusted to an amount not lower than a minimum amount of heat that is greater than zero;
means for detecting whether the current temperature is elevated by at least a minimum elevation level above the target temperature due to a heat influence of the subject; and
means for controlling the formation of vapor to maintain the target humidity based on the current temperature, wherein, responsive to the current temperature within the interface means being elevated by at least the minimum elevation level above the target temperature due to the heat influence of the subject, the formation of vapor is further controlled to maintain the target humidity as if the current temperature were equal to the target temperature, thereby inhibiting condensation from forming along the subject interface by the humidified, pressurized flow of breathable gas between the pressure generator and the airway of the subject.

14. The system of claim 13, wherein the target humidity is a target relative humidity percentage.

15. The system of claim 13, wherein the minimum amount of heat generated to heat the humidified, pressurized flow of breathable gas is based on an ambient temperature.

16. The system of claim 13, wherein, responsive to the current temperature no longer being elevated by at least the minimum elevation level above the target temperature due to the heat influence of the subject, the means for controlling the formation of vapor to maintain the target humidity reverts to being based on the current temperature.

17. The system of claim 16, wherein the means for controlling the formation of vapor to maintain the target humidity is further based on a detection of the subject being actively engaged with the system, wherein the detection is based on one or more output signals.

18. The system of claim 13, wherein the means for detecting whether the current temperature is elevated by at least the minimum elevation level above the target temperature due to the heat influence of the subject is configured to determine the minimum elevation level based on one or more of a type of interface means appliance, a location of one of the means for generating output signals, a flow rate of the pressurized flow of breathable gas, or an ambient temperature.

* * * * *